United States Patent
Davis (10) Patent No.: US 10,549,083 B2
(45) Date of Patent: Feb. 4, 2020

(54) LARGE BORE ENTERAL CONNECTOR

(71) Applicant: NEOMED, INC., Woodstock, GA (US)

(72) Inventor: Benjamin M. Davis, Woodstock, GA (US)

(73) Assignee: NeoMed, Inc., Woodstock, GA (US)

( * ) Notice: Subject to any disclaimer, the term of this patent is extended or adjusted under 35 U.S.C. 154(b) by 14 days.

(21) Appl. No.: 15/405,767

(22) Filed: Jan. 13, 2017

(65) Prior Publication Data

US 2017/0203086 A1 Jul. 20, 2017

Related U.S. Application Data

(60) Provisional application No. 62/279,156, filed on Jan. 15, 2016.

(51) Int. Cl.
| | |
|---|---|
| *A61M 25/16* | (2006.01) |
| *A61M 25/18* | (2006.01) |
| *A61M 39/10* | (2006.01) |
| *A61J 15/00* | (2006.01) |

(52) U.S. Cl.
CPC .......... *A61M 39/10* (2013.01); *A61J 15/0076* (2015.05); *A61M 2039/1033* (2013.01)

(58) Field of Classification Search
CPC ............. A61J 15/0076; A61J 15/0026; A61M 2039/1033; A61M 39/10; A61M 2202/0482
See application file for complete search history.

(56) References Cited

U.S. PATENT DOCUMENTS

| | | | |
|---|---|---|---|
| 4,969,565 | A | 11/1990 | Justal et al. |
| 5,242,429 | A | 9/1993 | Nwaneri et al. |
| 7,530,977 | B2 | 5/2009 | Lodi |
| 8,292,875 | B2 | 10/2012 | Kennard |
| 8,372,057 | B2 | 2/2013 | Cude et al. |
| 8,613,738 | B2 | 12/2013 | Mantell |
| 9,579,497 | B2 | 2/2017 | Cude et al. |
| 2005/0033269 | A1 | 2/2005 | Decaria |
| 2005/0245899 | A1 | 11/2005 | Swisher |
| 2007/0076401 | A1 | 4/2007 | Carrez et al. |
| 2008/0103486 | A1 | 5/2008 | Owens |
| 2008/0140020 | A1 | 6/2008 | Shirley |
| 2008/0140055 | A1 | 6/2008 | Shirley |

(Continued)

FOREIGN PATENT DOCUMENTS

| | | |
|---|---|---|
| EP | 2251061 A2 | 11/2010 |
| WO | 9109643 A1 | 7/1991 |

(Continued)

OTHER PUBLICATIONS

Invitation to Pay Additional Fees for PCT/US2017/013382; dated May 3, 2017; 16 pgs.

(Continued)

*Primary Examiner* — Rebecca E Eisenberg
(74) *Attorney, Agent, or Firm* — Dority & Manning, P.A.

(57) ABSTRACT

An enteral feeding connector, coupling or syringe tip configured for compatibility with blenderized feeding applications. The connector, coupling or syringe tip has a minimum internal bore dimension greater than the standard ENFit coupling specifications, to provide improved delivery of blenderized food.

14 Claims, 9 Drawing Sheets

(56) References Cited

U.S. PATENT DOCUMENTS

| | | | |
|---|---|---|---|
| 2008/0183153 A1* | 7/2008 | Enns | A61M 39/10 604/533 |
| 2008/0312640 A1 | 12/2008 | Grant | |
| 2010/0022966 A1 | 1/2010 | Kennard | |
| 2012/0022457 A1 | 1/2012 | Silver | |
| 2012/0029481 A1 | 2/2012 | Pech et al. | |
| 2012/0035593 A1 | 2/2012 | Lair | |
| 2012/0203171 A1* | 8/2012 | Williams | A61J 15/0015 604/96.01 |
| 2012/0310177 A1 | 12/2012 | Becker et al. | |
| 2014/0066840 A1 | 3/2014 | Mantell | |
| 2016/0089528 A1 | 3/2016 | Schuessler | |
| 2016/0158110 A1 | 6/2016 | Swisher et al. | |
| 2016/0175201 A1 | 6/2016 | Schuessler | |
| 2017/0156988 A1* | 6/2017 | Swisher | A61J 15/0076 |

FOREIGN PATENT DOCUMENTS

| | | |
|---|---|---|
| WO | 2004064895 A2 | 8/2004 |
| WO | 2015034045 A1 | 3/2015 |

OTHER PUBLICATIONS

"Qosina Catalog 2016," published by Qosina, 2002-Q Orville Drive North, Ronkonkoma, NY 11779; 2016; 4 pages.
Qosina Large Bore Connector, Product #98652, https://www.qosina.com/large-bore-male-connector-clear-98652; commercially released Oct. 2000; 2 pages.

* cited by examiner

|  | ID defined in ISO 80369-3 Standard | Modified ID |
|---|---|---|
| Male ENFit Coupling | $X_{MC} = 2.90$ mm | $X_1$ & $X_3 = 5.64$ mm |
| Female ENFit Coupling | $X_{CS} = 2.90$ mm | $X_2 = 5.26$ mm |

|  | Area defined in ISO 80369-3 Standard | Modified Area |
|---|---|---|
| Male ENFit Coupling | $A_{MC} = 6.61$ mm$^2$ | $A_1$ & $A_3 = 24.98$ mm$^2$ |
| Female ENFit Coupling | $A_{CS} = 6.61$ mm$^2$ | $A_2 = 21.73$ mm$^2$ |

FIG. 11

LARGE BORE ENTERAL CONNECTOR

CROSS-REFERENCE TO RELATED APPLICATION

This application claims the priority benefit of U.S. Provisional Patent Application Ser. No. 62/279,156 filed Jan. 15, 2016, the entirety of which is hereby incorporated by reference herein.

TECHNICAL FIELD

The present invention relates generally to the field of connectors for feeding tubes, and more particularly to connectors for large bore feeding tubes for blenderized feeding applications.

BACKGROUND

Enteral feeding systems are generally utilized to supply nutrition to the human gastrointestinal tract through an enteral feeding tube. For example, in the field of enteral feeding systems, optional delivery methods can include an enteral pump, syringe pump, or gravity feed delivery system. Optionally, a gastric pressure relief system can be used in conjunction with enteral feeding systems, for example when the subject is susceptible to reflux.

Enteral syringes and other components having enteral-only couplings or connectors conforming to the new ISO 80369-3 design standard (commonly known as ENFit®) have been known to restrict and limit the flow of some feeds used with enteral feeding systems, for example, blenderized foods. In particular, gravity feed systems utilizing the new ISO 80369-3 standard components with blenderized foods typically lack some functionality, for example, as the new ISO 80369-3 standard includes conduits that substantially restrict the flow of high viscosity fluids such as blenderized foods.

Thus, it can be seen that needs exist for improved couplings and connectors for enteral syringes and other components that reduce their resistance to the flow of high viscosity fluids, for example, when using the enteral pump, syringe pump, gravity feed delivery system, or other various delivery systems. It is to the provision of a large bore enteral connector providing for the adequate flow of high viscosity fluids therethrough that the present invention is primarily directed.

SUMMARY

In example embodiments, the present invention provides a large bore enteral connector configured for compatibility with blenderized feeding applications, for example, to support high viscosity fluids such as blenderized foods.

In one aspect, the present invention relates to a large bore enteral connector including a first end having an outer circumferential collar including an internal threaded portion defining a least one thread, and a second end including a tube coupling member for sealingly engaging with an end of a feeding tube. In example embodiments, the tube coupling member includes an internal conduit axially extending through the entirety of the connector between the first and second ends.

In example embodiments, the internal conduit defines an inner diameter of between about 3-6 millimeters. In one example embodiment, the internal conduit defines an inner diameter of about 5.64 millimeters. In example embodiments, the tube coupling member is sized and shaped for sealingly engaging an internal periphery portion of the feeding tube. Optionally, the tube coupling member is sized and shaped for sealingly engaging an external periphery portion of the feeding tube. In example embodiments, the tube coupling member is generally shaped and sized to be sealingly engagable with feeding tubes of French gauges between 10-34.

In another aspect, the present invention relates to a syringe having a syringe tip extending therefrom, the syringe tip having exterior features compatible with the ISO 80369-3 design standard, and a conduit extending through the entirety of the syringe tip and defines an inner diameter of between about 3-6 millimeters. In example embodiments, the inner diameter of the conduit of the syringe tip is about 5.26 millimeters. In example embodiments, the syringe tip is configured for sealingly engaging with an outer circumferential collar having an internal threaded portion defining at least one thread. In example embodiments, an end surface of the syringe tip is generally sealingly engaged with an internal seating surface of the outer collar. In example embodiments, the syringe tip includes an angled surface formed at an end portion thereof, and wherein a central collar is formed with the internal seating surface to provide a sealed connection when the syringe tip is removably coupled with the outer collar.

In another aspect, the present invention relates to a connector for attachment to a feeding tube, the connector including a first end having an exterior shape and features compatible with design standard ISO 80369-3; and a second end including a coupling member for sealing engagement with a feeding tube. In example embodiments, the first end includes an outer collar having an internal threaded portion including one or more threads. In example embodiments, the second end includes a conduit axially extending through the entirety of the connector and defining a minimum inner diameter. In example embodiments, the minimum inner diameter is generally between about 3-6 millimeters. In example embodiments, the minimum inner diameter is about 5.64 millimeters. In example embodiments, the first end includes a cylindrical female member having a conduit extending therethrough and defining an inner diameter. In example embodiments, the inner diameter of the conduit of the cylindrical female member is between about 3-6 millimeters. In example embodiments, the inner diameter of the conduit of the cylindrical female member is about 5.26 millimeters. In example embodiments, the coupling member of the second end is configured for sealingly engaging an internal periphery portion of the feeding tube. In example embodiments, the coupling member of the second end is configured for sealingly engaging an outer periphery portion of the feeding tube.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-10 show a plurality of components for blenderized feeding applications including large bore connectors, syringes comprising a large bore formed within the tip thereof, and a feeding tube for coupling engagement with the large bore connectors and the syringe tips.

According to example embodiments, the present invention comprises a large bore enteral coupling or connector 10, 100 that is compatible with blenderized feeding. As depicted in FIG. 3, the connector 10 comprises a first end 12 for removably coupling and providing sealing engagement with a syringe tip FC of a syringe S and a second end 14 for coupling with an end of a feeding tube FT (see FIG. 2). In example embodiments, the first end 12 of the connector 10 generally comprises a modified male ENFit coupling, for example, having a collar 30 comprising an internal threaded portion including threads 32 for removable engagement with a pair of lugs R provided on the syringe tip FC of the syringe S (see FIG. 2). The second end 14 of the connector 10 is configured such that the feeding tube FT is fitted around an outside periphery thereof (see FIGS. 2-3). For example, according to one example form, the second end 14 comprises a tube coupling member 34 that defines a central conduit 20 (extending entirely through the connector 10). The tube coupling member 34 comprises an outer peripheral engagement surface 35, and a collar portion 36 is generally offset from the second end 14 and extends entirely around the engagement surface 35. As such, the feeding tube FT (e.g., the inner peripheral surface formed by the conduit) is generally configured for frictional engagement with the outer periphery 35 of the coupling member 34. Optionally, the engagement surface 35 can comprise one or more barbed features to securely capture and seal with the feeding tube. In example embodiments, the collar portion 36 comprises an abutment surface 40, which is generally oriented perpendicular relative to the outer periphery 35 to allow for abutment with the end of the feeding tube FT. As will be described below, the feeding tube FT can be sealingly engaged with the connector 10.

Optionally, a channel 42 is formed within a portion of the connector 10 (e.g., generally near a midpoint between the ends 12, 14) for receiving a tether or other ring-like member, for example, to which a portion of the tether extending therefrom could be used to capture a cap or closure (see FIGS. 4-5, 7-10).

Figure 1:
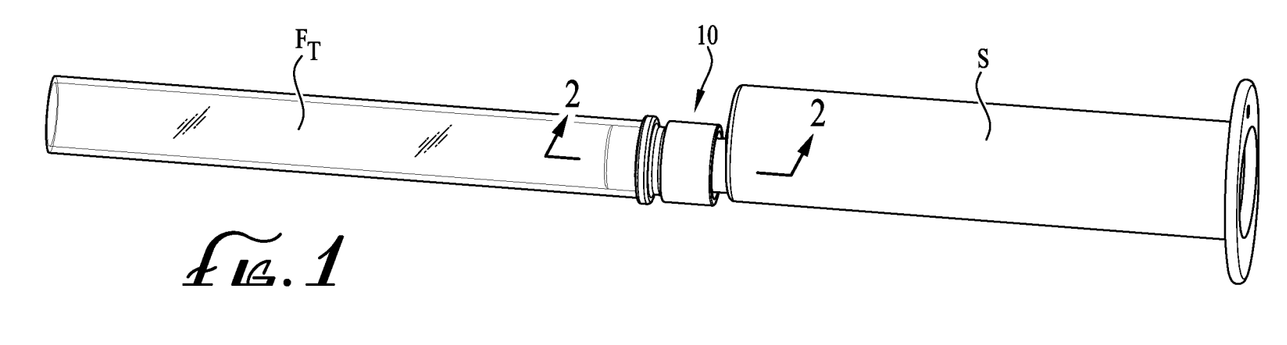
FIG. 1 is a perspective view of a large bore connector according to an example embodiment of the present invention, the large bore connector providing coupling engagement between a syringe and a feeding tube.
Figure 2:
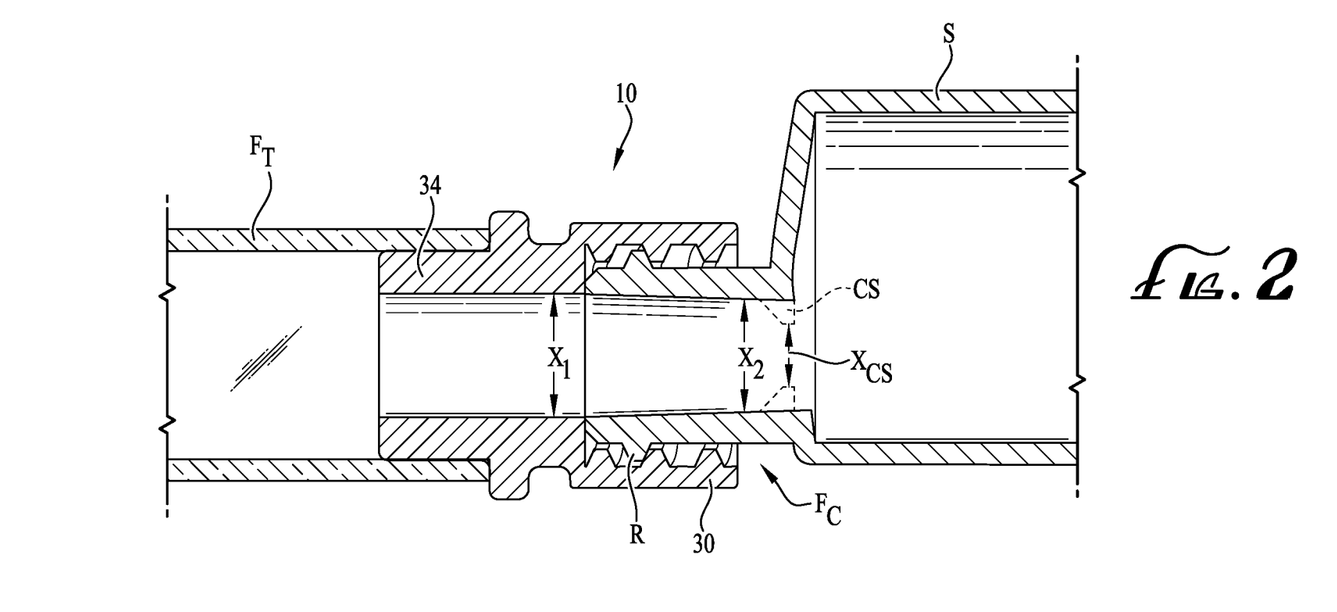
FIG. 2 is a cross-sectional view of the large bore connector, feeding tube and syringe taken along line 2-2 of FIG. 1.
Figure 3:
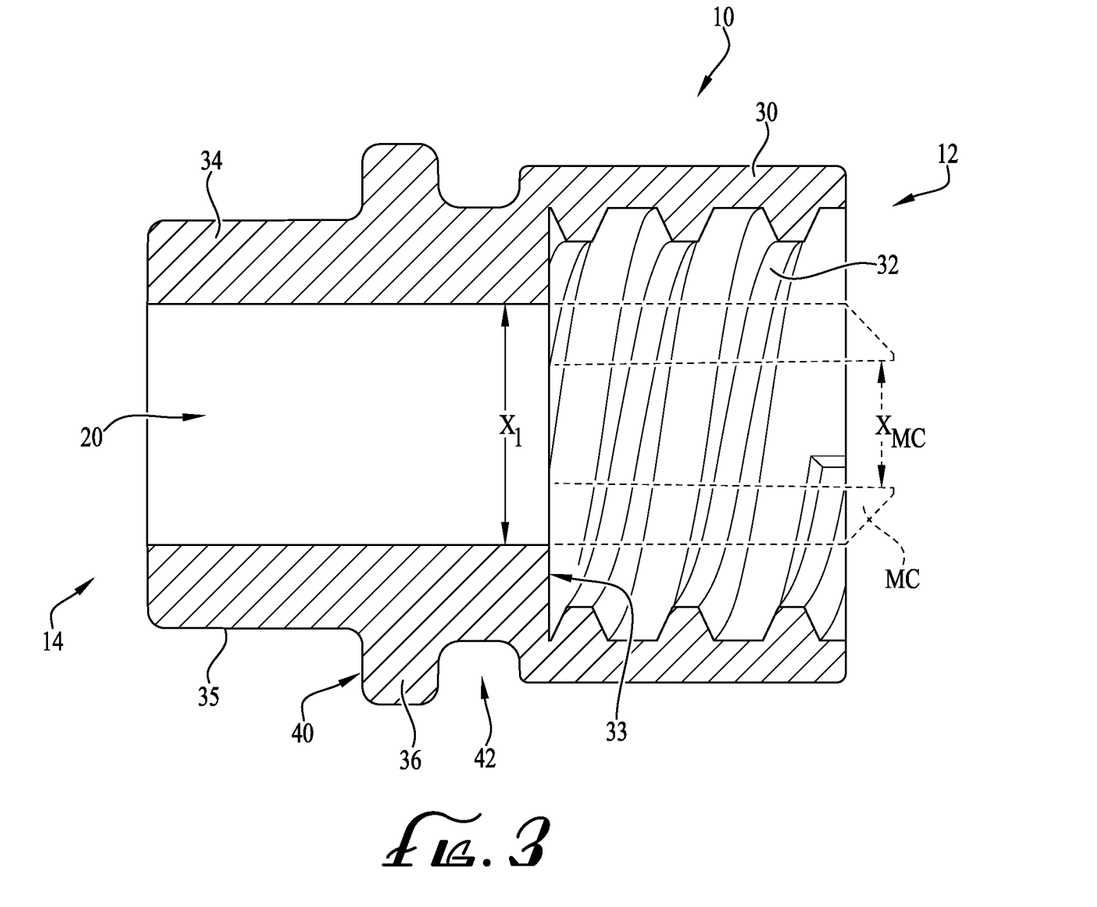
FIG. 3 is a cross-sectional view of the connector of FIG. 2.
Figure 4:
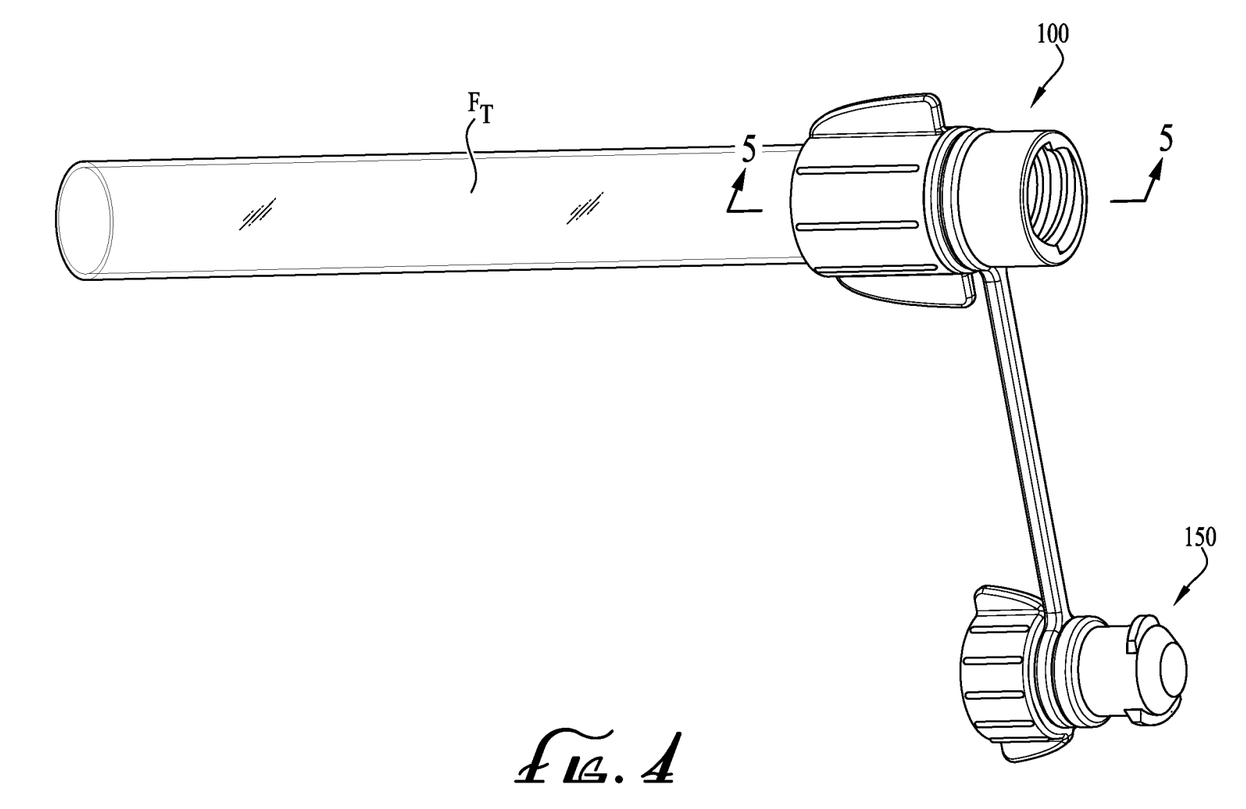
FIG. 4 is a perspective view of a large bore connector coupled to an end of a feeding tube according to another example embodiment of the present invention, the large bore connector comprising a cap tethered thereto.

As depicted in FIGS. 2-3, the size of the conduit 20 of the connector 10 is substantially larger than the conduit of the male coupling defined in the ISO 80369-3 design standard. For example, with reference to FIG. 3, the conduit 20 defines an inner diameter $X_1$, which is sized to be between about 3-6 millimeters, for example, about 5.64 millimeters according to one example embodiment. For comparison purposes, a male coupling MC defined in the ISO 80369-3 design standard and shown in dashed lines (for illustration purposes only), defines an inner diameter $X_{MC}$ of about 2.90 millimeters. Accordingly, the minimum inner diameter $X_1$ of the conduit 20 of the connector 10 is generally between about 0.10-3.10 millimeters larger, for example by about 2.74 millimeters larger than the inner diameter of the conduit defined by the male coupling MC referenced in the ISO 80369-3 design standard. Preferably, the increase in the inner diameter of the conduit reduces the restriction on the flow of high viscosity fluids, for example, blenderized foods.

As depicted in FIG. 2, to assist in minimizing the restriction of high viscosity fluids flowing to/from the syringe S, the syringe tip FC comprises a modified female ENFit coupling, for example, which comprises a substantially uniform conduit having an inner diameter $X_2$ that is generally similar to the inner diameter $X_1$ of the conduit 20 of the connector 10. In example embodiments, the inner diameter $X_2$ of the syringe tip FC is between about 3-6 millimeters, for example, about 5.26 millimeters according to one example embodiment of the present invention. For comparison purposes, an inner collar CS of the female ENFit coupling defined in the ISO 80369-3 design standard and shown in dashed lines (for illustration purposes only), defines an inner diameter $X_{CS}$ of about 2.90 millimeters. Accordingly, the minimum inner diameter of the syringe tip FC of the syringe S is generally about 2.36 millimeters larger than the inner diameter $X_{CS}$ of the inner collar CS that is defined by the female ENFit coupling referenced in the ISO 80369-3 design standard. Preferably and a similarly recited above, the increase in the inner diameter of the conduit of the syringe tip FC is less restrictive on the flow of high viscosity fluids, for example, blenderized foods.

In example embodiments, the minimum inside diameter or lumen dimension of the coupling, connector or syringe tip of the present invention is preferably configured to be compatible with blenderized food of various forms. According to example embodiments, the inner diameters $X_1$, $X_2$, and $X_3$ of the conduits or bores defined therein, respectively, is at least about 3.0 millimeters, or at least about 3.5 millimeters, more preferably at least about 4 millimeters, more preferably at least about 4.5 millimeters, more preferably at least about 5 millimeters, for example about 5.26 millimeters in an example embodiment, and about 5.64 millimeters in an another example embodiment.

Optionally, the first end 12 of the connector 10 (or collar 30) may be generally flared or tapered to comprise a substantially wider end that tapers towards a central axis that defines a dimension that is generally within the range for providing coupling engagement with the syringe tip FC, for example, wherein the outer dimensions of the syringe tip FC are generally sized according to ENFit standards. In some example embodiments, the connector 10 comprises a tapered receiver that tapers from an outer receiver dimension greater than that of a standard ENFit coupling to an inner receiver dimension generally equal to that of a standard ENFit coupling. According to example embodiments of the present invention, the engagement portions or mating surfaces of the connector 10 and the syringe tip FC are compatible to connect with connectors of the ISO 80369-3 design standard.

Figure 5:
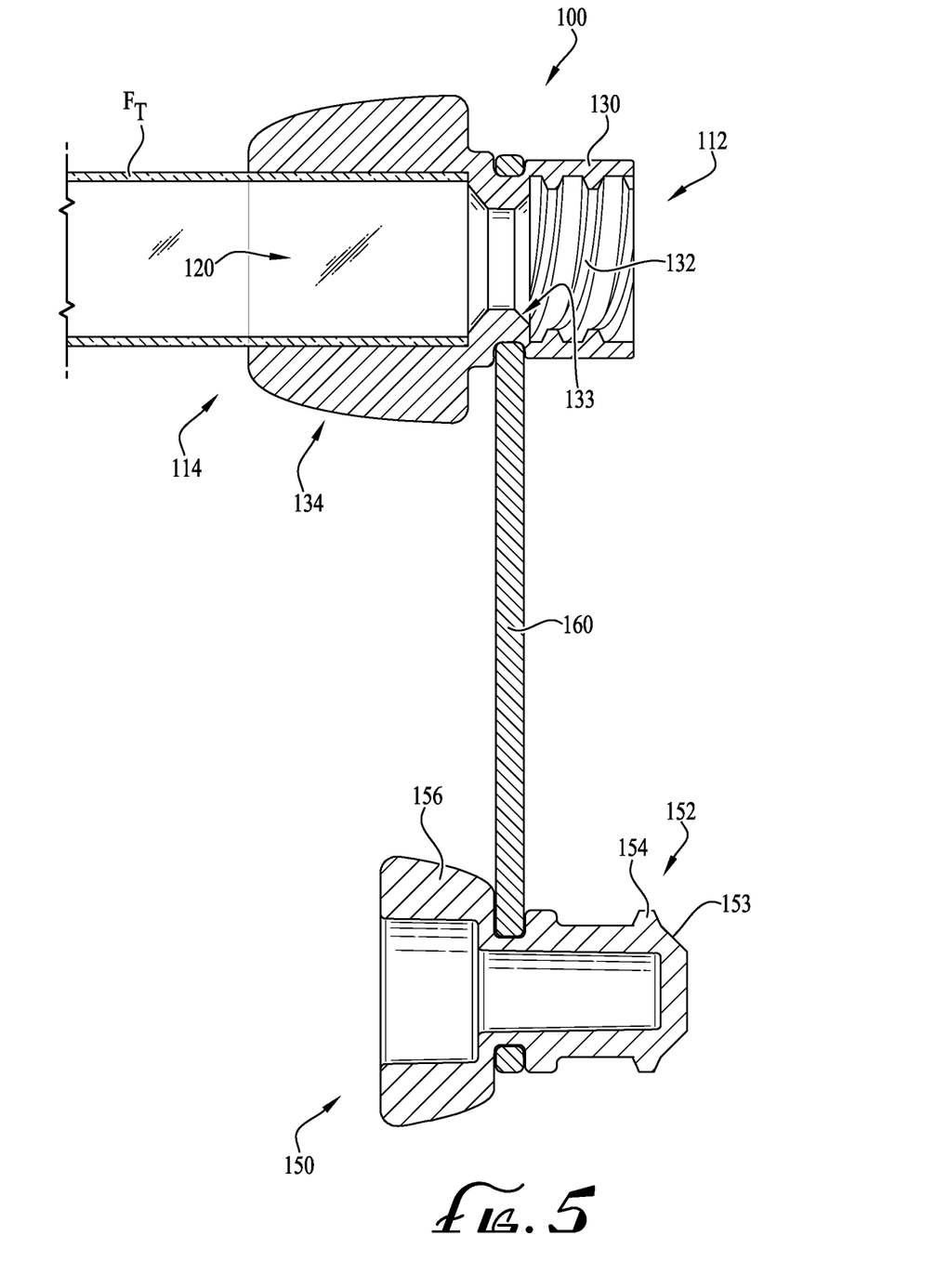
FIG. 5 is a cross-sectional view of the large bore connector, feeding tube, cap and tether taken along line 5-5 of FIG. 4.
Figure 6:
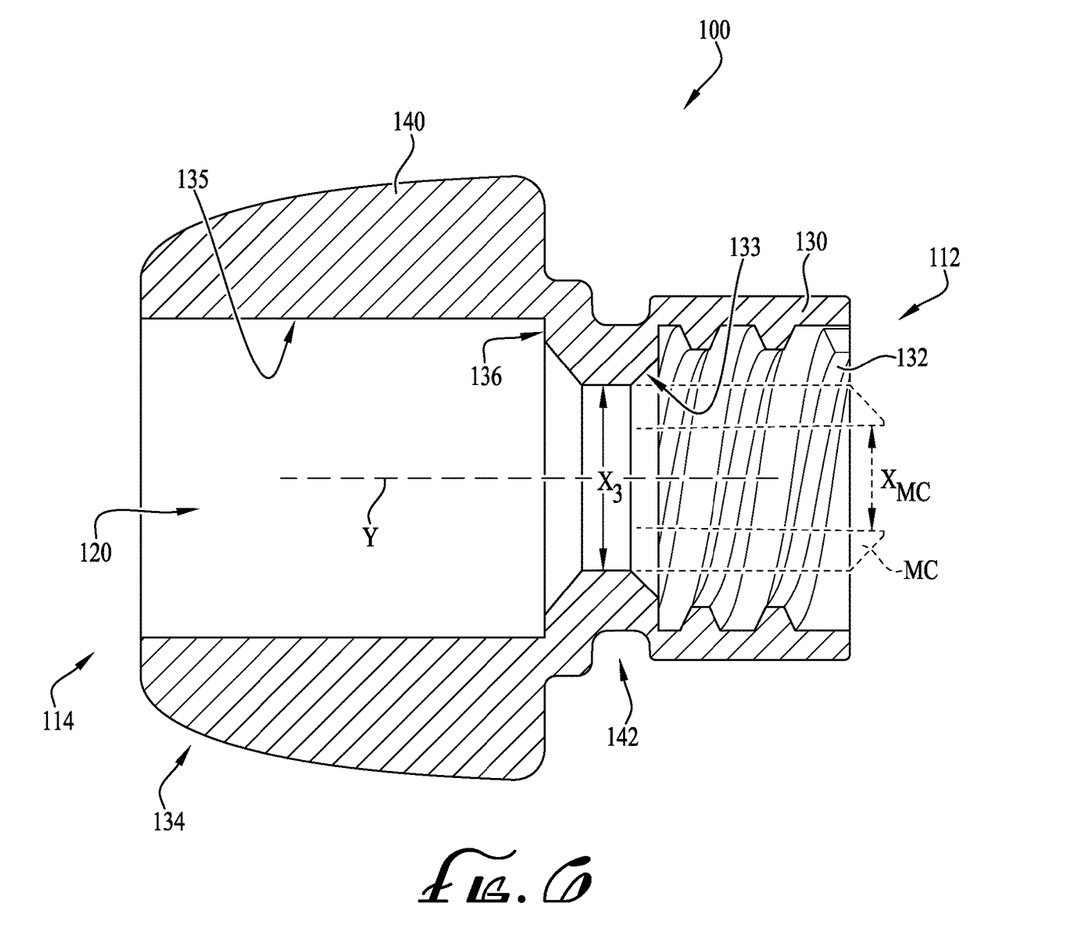
FIG. 6 is a cross-sectional view of the large bore connector of FIG. 5.

As depicted in FIGS. 4-10 and according to another example embodiment of the present invention, an outer or exterior portion of the feeding tube FT is configured for removable engagement with the second end 14 of the connector 100, for example, rather than an inner or interior surface of the feeding tube being engaged with the second end 14. For facilitating the engagement of the end of the feeding tube FT and the flow of blenderized food therethrough, a conduit 120 (oriented axially relative to the ends 112, 114 of the connector 100) extends entirely through the connector 100. For example, as depicted in FIGS. 5-6, the first end 112 is substantially similar to the first end 12 of the connector 10, for example, whereby the first end 112 comprises a collar 130 comprising an internally threaded portion defining one or more threads 132 for providing interengagement with the ribs R of the syringe tip FC, for example, to provide for sealingly engaging a syringe tip FC of a syringe S. Optionally, other modified female ENFit connectors or couplings (in addition to a syringe tip FC) can be utilized for connection with the first ends 12, 112 of the connectors 10, 100. For example, according to some example embodiments of the present invention, an extension set or member can be interconnected in the feeding system, for example, whereby one of the ends of the feeding tube comprises a connector comprising a first end having a modified female ENFit coupling and defining an inner diameter $X_2$ of about 5.26 millimeters, and a second end for engagement with the end of the feeding tube. The other end of the feeding tube, according to one example embodiment, comprises one of the connectors 10, 100 as described herein. Thus, when a greater extension is needed between the feeding tube FT connected to the patient and the syringe S, an extension comprising compatible end connectors can be used as desired.

Referring back to FIG. 6, the second end 114 comprises a coupling 134 for receiving an end of the feeding tube FT. In example embodiments, the coupling 134 comprises an outer shell comprising a pair of wings or gripping features 140, and an inner engagement surface 135 and abutment surface 136 are formed within the coupling and defining the conduit 120. According to example embodiments, an end of the feeding tube FT is generally fitted within the conduit 120 such that an outer or exterior portion of the feeding tube FT is frictionally engaged with the inner engagement surface 135. In example embodiments, the feeding tube is generally fully seated with the coupling 134 once the end of the feeding tube FT is abutting the abutment surface 136. Optionally, barbs or other engagement features or components can be formed within at least a portion of the inner engagement surface 135, for example, to provide sealing engagement between the end of the feeding tube FT and the coupling 134.

In example embodiments, the gripping features 140 can benefit the user during installation or removal of the feeding tube FT, syringe tip FC, or other modified female ENFit coupling formats. In example embodiments, two gripping features 140 are generally formed on an outer exterior portion of the coupling 134 at diametrically opposing positions, for example, which generally extend from the second end 114 to a portion of the connector generally near the midpoint thereof. In example embodiments, the gripping features 140 are at least partially radiused and generally transition in their height along the extension thereof. Optionally, only one or more than two gripping features can be formed as desired along an outer periphery portion of the connector 100 as desired.

As depicted in FIG. 6, a male coupling MC defined in the ISO 80369-3 design standard and shown in dashed lines defines an inner diameter $X_{MC}$ of about 2.90 millimeters. In example embodiments, rather than having the substantially reduced inner diameter $X_{MC}$ of the male coupling MC, a central collar is formed within the connector and defined between the first and second ends 112, 114. In example embodiments, the central collar defines a minimum inner diameter $X_3$ of between about 3-6 millimeters, for example, about 5.64 millimeters according to one example embodiment. Accordingly, the minimum inner diameter of the conduit 20 of the connector 100 is generally about 2.74 millimeters larger than the inner diameter of the conduit defined by the male coupling MC referenced in the ISO 80369-3 design standard. Preferably, the increase in the inner diameter of the conduit reduces the restriction on the flow of high viscosity fluids, for example, blenderized foods.

Figure 10:
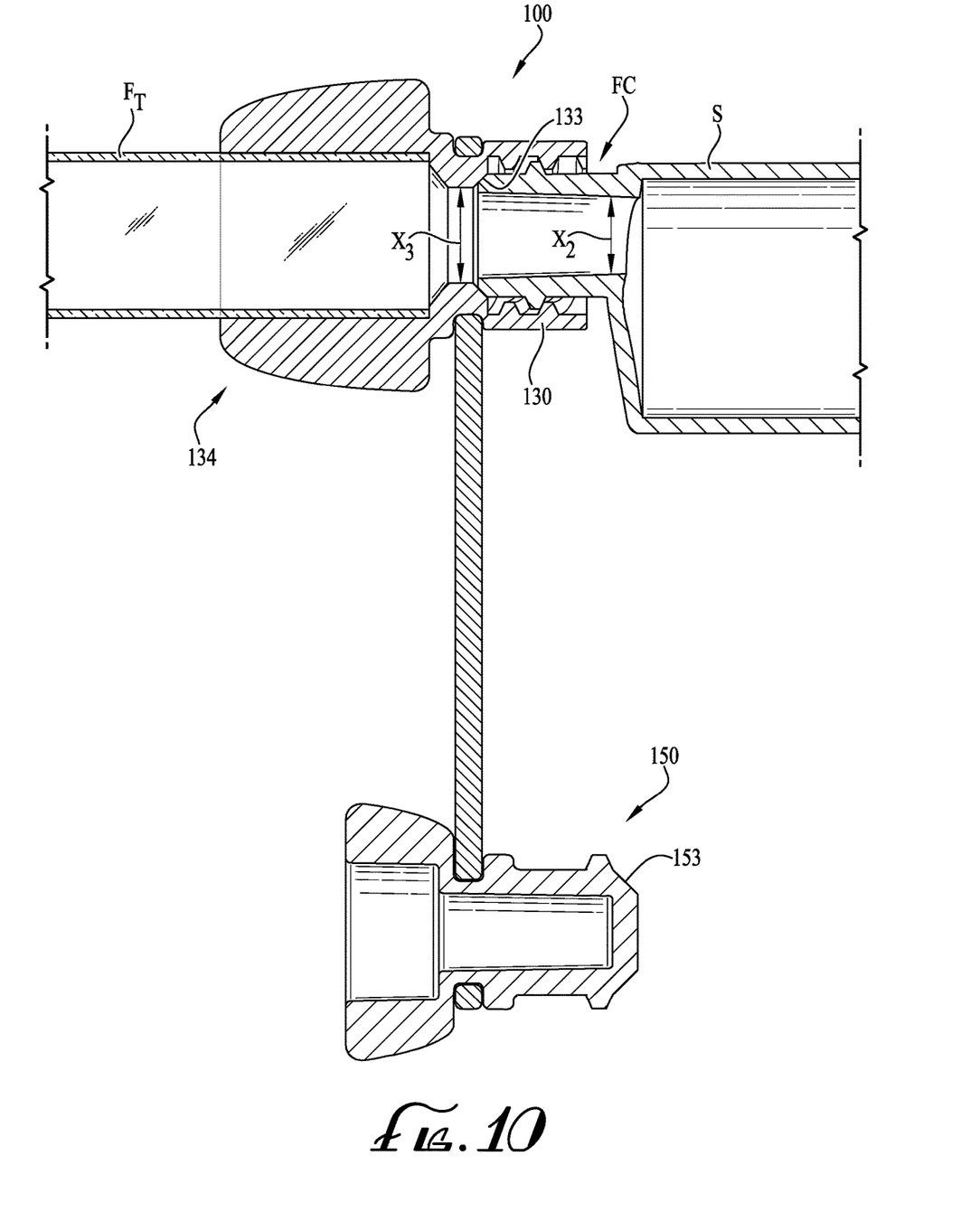
FIG. 10 shows a cross-sectional view of the large bore connector, the syringe, and the feeding tube taken along line 10-10 of FIG. 9.

According to example embodiments, the central collar of the coupling 100 comprises an angled engagement or sealing surface 133, which preferably provides for sealing engagement with a chamfered edge around the end tip of the syringe tip FC (see FIG. 10). In example embodiments, the angles of the angled engagement surface 133 and the chamfered edge of the syringe tip FC are generally complementary, for example, such that they generally seat or sealingly engage each other. Accordingly, the angled sealing surface 133 of the connector 100 provides an adequate seal with the syringe tip when the two are coupled together. In example forms, the angled sealing surface 133 of the connector 100 is oriented at an angle of about 45 degrees relative to an elongate axis Y extending through the bore 120 of the connector. Optionally, the angled sealing surface 133 may be oriented at other angles, for example, at about 20 degrees, about 30 degrees, or for example between about 40-50 degrees. In the same manner, a closure 150 can comprise an angled end surface 153, which is substantially complementary to the angle of the angled engagement surface 133, for example, such that a seal is provided when the closure 150 is removably coupled with the first end 112 of the connector 100.

Figure 7:
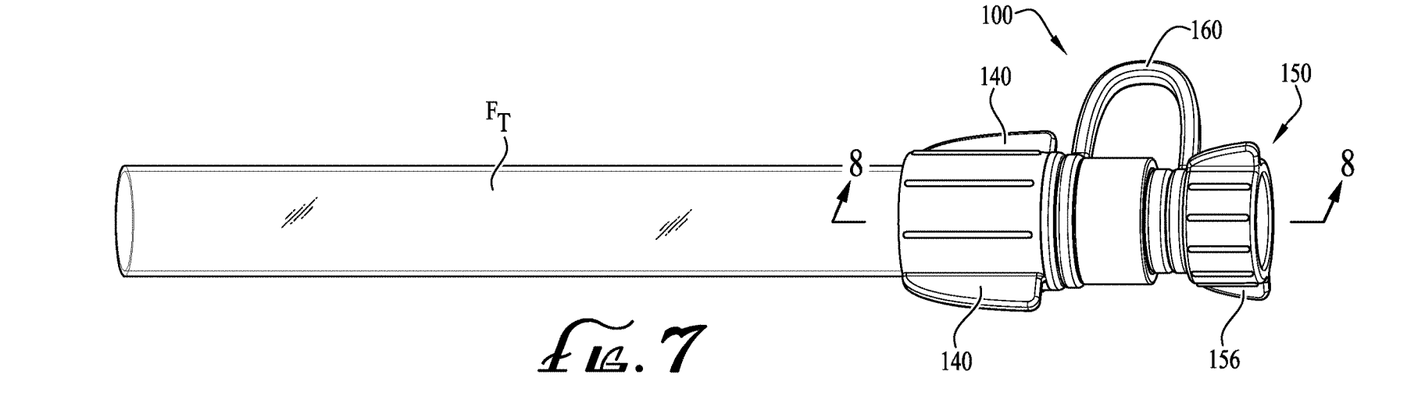
FIG. 7 is a perspective view of a large bore connector coupled to an end of a feeding tube of FIG. 4, and showing the cap removably coupled within the large bore connector.
Figure 8:
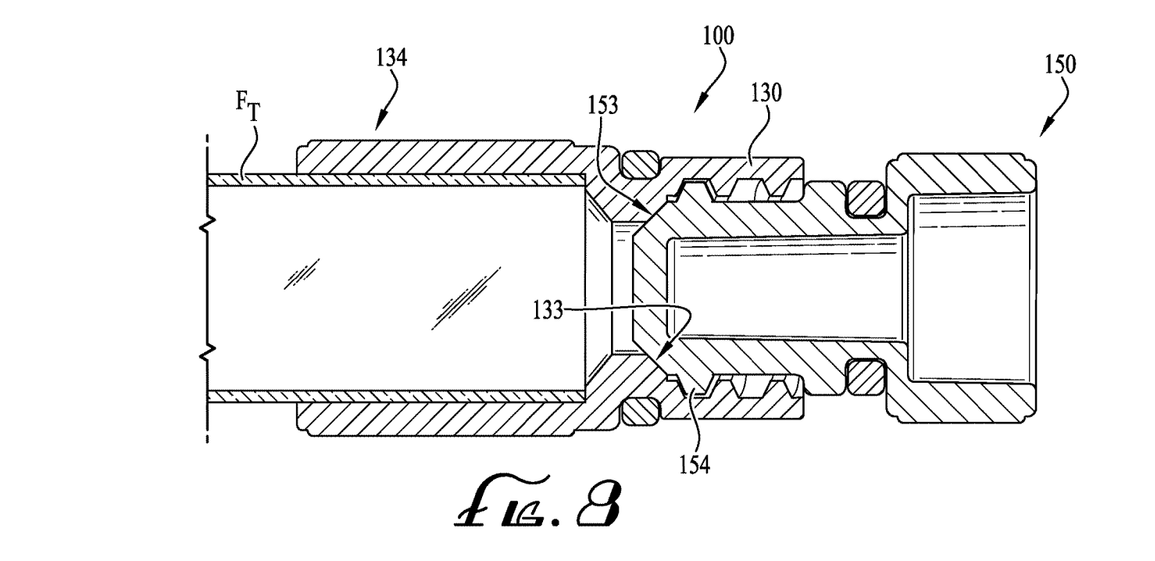
FIG. 8 is a cross-sectional view of the large bore connector, feeding tube, cap and tether taken along line 8-8 of FIG. 7.
Figure 9:
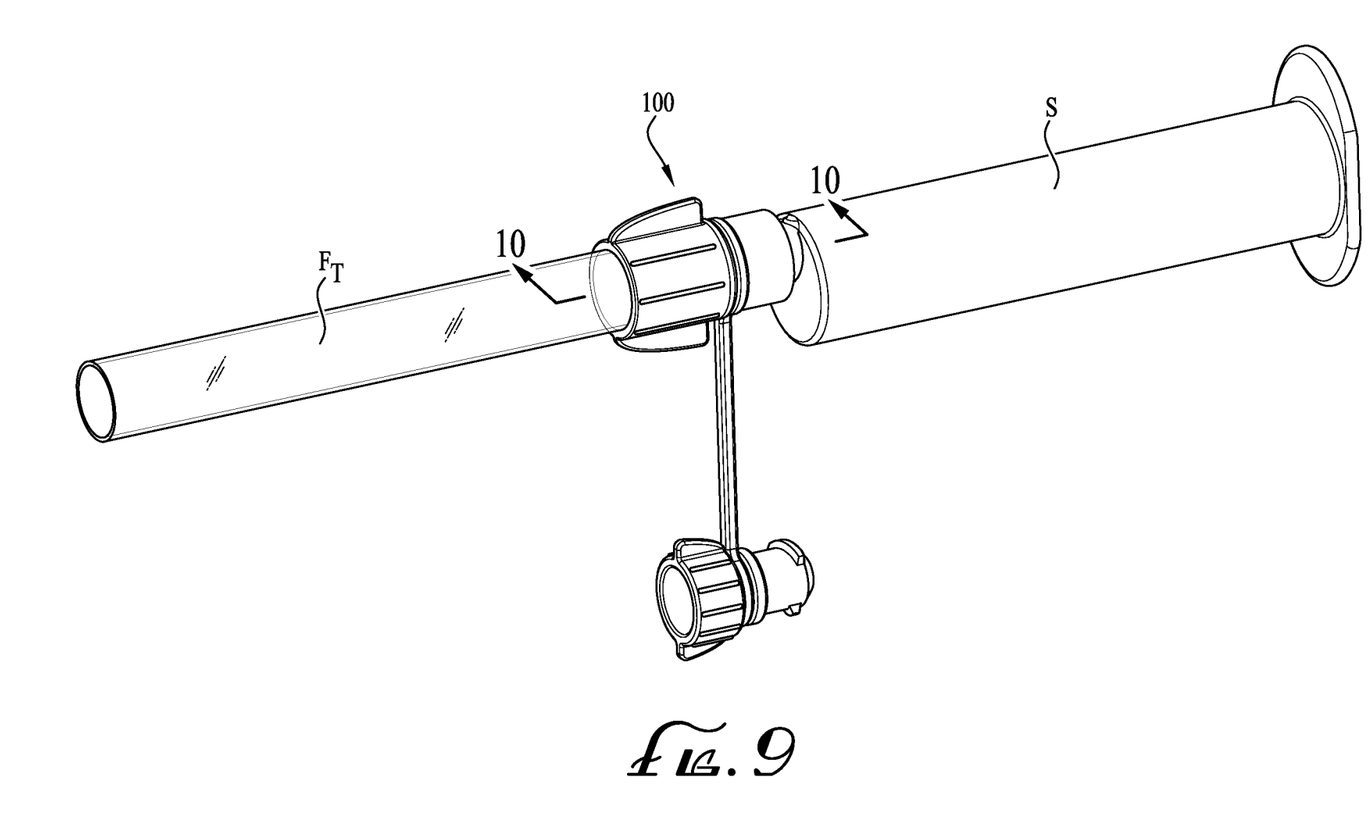
FIG. 9 is a perspective view of the large bore connector and feeding tube of FIG. 4, and showing a syringe coupled to a portion of the connector.

According to some example embodiments, as similarly described above, the connector 100 can comprise a channel 142 formed along at least a portion of the outer periphery of the connector, for example, such that a cap or closure 150 can be coupled with the connector 100 by a tether 160. In example embodiments, the closure comprises a coupling portion 152 comprising engagement ribs 154 for coupling engagement with the threads 132 of the internal threaded portion of the collar 130. Optionally, partial threads (e.g., lugs) or one or more helical threads (e.g., fully threaded) may be provided on the coupling portion 152, for example, rather than the depicted engagement ribs 154. An end opposite of the engagement ribs 154 comprises a pair of wings or gripping features 156, for example, to facilitate the gripping thereof and for attachment/removal from the collar 130 of the first end 112. Preferably, the gripping features 156 can be shaped and sized as desired. For example, as depicted in FIG. 7, when the closure 150 is sealingly engaged with the collar 130, the gripping features 156 of the closure 150 slowly transition in height from a first height that is at least partially greater than a second height. Further moving along the connector, the gripping features 140 transition from a first height to a second height, for example, wherein the first height is at least partially greater than the second height. Thus, when the closure 150 is sealingly engaged with the first end 112 of the connector 100, the gripping features 156, 140 generally define an undulating or saw-tooth configuration such that the gripping features transition from a first height to a second height, and back to a first height and further transitioning to the second height. Optionally, the extension and orientation of the gripping features can be configured as desired. For example, according to an example embodiment, the gripping features 156 can transition from the second height to a first height, such that when the closure 150 is sealingly engaged with the first end 112, the gripping features 156, 140 are at least partially symmetrical whereby the shorter second heights are defined at the outer ends thereof.

In example embodiments, a plurality of different sized feeding tubes FT can be used for coupling engagement with the connectors 10, 100 of the present invention. For example, according to example embodiments, the feeding tubes are generally sized between a French gauge of about 10-34, for example, between about 14 Fr-32 Fr according to example embodiments of the present invention. In example embodiments, the specific size and dimensions of the second end 14, 114 of the connector 10, 100 can be adjusted based on the size of the feeding tube, and for example, based on whether the outer periphery or inner diameter of the end of the feeding tube FT is intended for engagement with the second end 14, 114.

Figure 11:
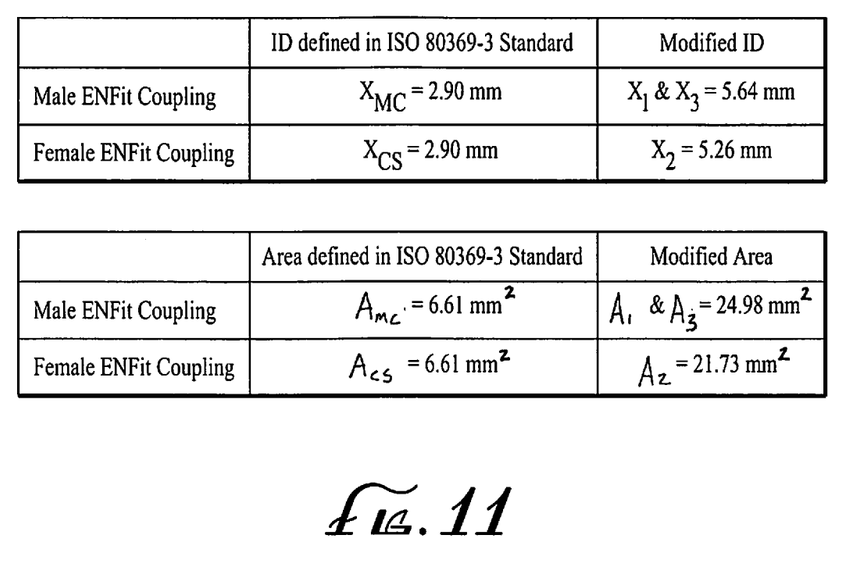
FIG. 11 shows a chart showing the dimensions of the inner diameter and areas of the male and female ENFit couplings as defined in the ISO 80369-3 design standard, and the dimensions of the inner diameter and areas of the modified couplings of the connectors.

According to example embodiments and described above, the inner diameter of the connectors 10, 100 and syringe tip FC of the present invention are generally modified with respect to the dimensions defined by the ENFit standard (see ENFit design standard, ISO 80369-3, incorporated herein by reference). As shown in the chart of FIG. 11, the inner diameter and area of the male and female ENFit couplings according to the ISO 80369-3 design standard are shown. For example, the areas $A_{MC}$ and $A_{CS}$ taken at the inner diameters of $X_{MC}$ and $X_{CS}$ are both equal to 6.61 mm$^2$ (e.g., $A=\pi r^2$). Similarly, the modified inner diameters and areas are shown, which are substantially greater than the dimensions defined by the ENFit standard. For example, according to one example embodiment, $X_1$ and $X_3$ are about 5.64 millimeters (with the respective areas $A_1$ and $A_3$ being about 24.98 mm$^2$). And $X_2$ is about 5.26 millimeters (with the respective area $A_2$ being about 21.73 mm$^2$). As similarly recited above, the modified inner diameters can be varied as desired, for example, which are generally defined between about 3-6 millimeters. For example, according to one preferred embodiment, the modified inner diameter of the male coupling is about 5.64 millimeters, and the modified inner diameter of the female coupling is about 5.26 millimeters.

According to example embodiments, the present invention preferably expands or enlarges the conduits or through bores of the male and female ENFit couplings such that the female ENFit connector (e.g., the "giving side") is returned to a "male" connector and the male ENFit connector (e.g., the "patient access side" or "feeding tube side") is returned to a "female" connector. For example, as described above, by removal of the male coupling MC from the connector (see first ends 12, 112 comprising the collars 30, 130), the modified male ENFit coupling is returned to a "female" coupling and the modified female ENFit coupling is returned to a "male" coupling. Accordingly, the modified male ENFit coupling or "female" coupling is compatible for connection with ISO 80369-3 connectors (e.g., female ENFit couplings) and the modified female ENFit coupling or "male" coupling is compatible for connection with ISO 80369-3 connectors (e.g., male ENFit coupling). As such, according to example embodiments, the exterior or mating features of the modified male and female ENFit couplings as described herein are preferably connectable with each other (e.g., modified male ENFit coupling connectable with modified female ENFit coupling), and the modified male and female ENFit couplings are also connectable with the male and female ENFit connectors sized and shaped according to the ISO 80369-3 design standard.

According to example embodiments, the connectors as described herein preferably resist or prevent inadvertent misconnection with other coupling or connector formats, which could potentially lead to unintended or undesirable consequences. IN example embodiments, a misconnection analysis of the connectors 10, 100 as described herein are compared to various other coupling formats. For example, preferably the connector resists or prevents inadvertent misconnection with the other coupling formats. In example embodiments, the coupling formats that were tested for resisting and preventing inadvertent misconnection with the connectors 10, 100 include ISO80369-2 respiratory, ISO80369-3 enteral (male only), ISO80369-5 limb cuff, ISO80369-6 neuraxial, and ISO80369-7 introvascular and hypodermic.

The present invention also comprehends feeding syringes, feeding tubes and other components compatible with the above described blenderized feeding couplings, as well as methods of fabrication and use of the above described blenderized feeding couplings, such as for example by omission, removal or other modification of a standard ENFit connector and/or associated enteral feeding components. Components according to the present invention are optionally compatible with both gravity fed and bolus fed blenderized feeding applications, for example utilizing syringes, bags or other food storage and delivery applications. Optionally, a sieve or screen is provided for placement in the delivery path, for example in the syringe body, with openings sized to prevent passage of food particles larger than the minimum ID of the coupling or connector, to prevent clogging or blockage. In further example embodiments, an X-valve or slit membrane valve is optionally provided in the coupling lumen to prevent leakage or backflow.

While the invention has been described with reference to preferred and example embodiments, it will be understood by those skilled in the art that a variety of modifications, additions and deletions are within the scope of the invention, as defined by the following claims.

What is claimed is:

1. A large bore enteral connector comprising:
   a first end consisting of an outer circumferential collar having an internal threaded portion defining a least one thread; and
   a second end comprising a tube coupling member for sealingly engaging with an end of a feeding tube, the tube coupling member and the circumferential collar defining an internal conduit axially extending through the entirety of the connector between the first and second ends, wherein the internal conduit defines an inner clearance of between about 3-6 millimeters.

2. The large bore enteral connector of claim 1, wherein the internal conduit inner clearance defines an inner diameter of about 5.64 millimeters.

3. The large bore connector of claim 1, wherein the tube coupling member is sized and shaped for sealingly engaging an internal periphery portion of the feeding tube.

4. The large bore connector of claim 1, wherein the tube coupling member is sized and shaped for sealingly engaging an external periphery portion of the feeding tube.

5. The large bore connector of claim 1, wherein the tube coupling member is generally shaped and sized to be sealingly engagable with feeding tubes of French gauges between 10-34.

6. A syringe comprising a syringe tip extending therefrom, the syringe tip consists of an outer collar comprising mating features compatible with the ISO 80369-3 design standard, and a conduit extending through the entirety of the syringe tip and defines an inner diameter of between about 3-6 millimeters.

7. The syringe of claim 6, wherein the inner diameter of the conduit of the syringe tip is about 5.26 millimeters.

8. The syringe of claim 7, wherein the syringe tip is configured for sealingly engaging with an outer circumferential collar having an internal threaded portion defining at least one thread.

9. The syringe of claim 8, wherein an end surface of the syringe tip is generally sealingly engaged with an internal seating surface of the outer collar.

10. A connector for attachment to a feeding tube, the connector comprising:
    a first end consisting of an outer collar comprising features compatible with design standard ISO 80369-3; and
    a second end comprising a coupling member for sealing engagement with a feeding tube, wherein the first end and the second end define a conduit axially extending through the entirety of the connector and defining a minimum inner diameter and wherein the minimum inner diameter is generally between about 3-6 millimeters.

11. The connector of claim 10, wherein the collar comprising an internal threaded portion comprising one or more threads.

12. The connector of claim 10, wherein the minimum inner diameter is about 5.64 millimeters.

13. The connector of claim 10, wherein the coupling member of the second end is configured for sealingly engaging an internal periphery portion of the feeding tube.

14. The connector of claim 10, wherein the coupling member of the second end is configured for sealingly engaging an outer periphery portion of the feeding tube.

* * * * *